(12) United States Patent
Gent et al.

(10) Patent No.: US 6,494,076 B1
(45) Date of Patent: Dec. 17, 2002

(54) PENDULUM ROLLING RESISTANT TEST

(75) Inventors: Alan Neville Gent, Ravenna, OH (US); William Allen Arnold, Akron, OH (US); John Darrell Carter, Uniontown, OH (US); David Dale Gallagher, Marysville, OH (US); Robin Bovaird Steven, Dublin, OH (US); John James Gartland, Delaware, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/856,346

(22) PCT Filed: Dec. 22, 1998

(86) PCT No.: PCT/US98/27414

§ 371 (c)(1),
(2), (4) Date: Sep. 20, 2001

(87) PCT Pub. No.: WO00/37921

PCT Pub. Date: Jun. 29, 2000

(51) Int. Cl.[7] .................................................. G01N 3/56
(52) U.S. Cl. ............................................................. 73/9

(58) Field of Search ..................................... 73/9, 8, 10

(56) References Cited

U.S. PATENT DOCUMENTS

| 4,458,527 A | * | 7/1984 | McFarland et al. ............ 73/146 |
| 4,538,772 A | | 9/1985 | Davies ....................... 242/18 R |
| 5,029,837 A | * | 7/1991 | Uchiyama .................... 271/110 |
| 5,049,057 A | * | 9/1991 | Yamaguchi et al. ......... 264/340 |
| 5,635,623 A | | 6/1997 | Simon ............................. 73/9 |

FOREIGN PATENT DOCUMENTS

GB            903745 A      8/1962

* cited by examiner

Primary Examiner—Max Noori
(74) Attorney, Agent, or Firm—David E Wheeler; Richard B O'Planick

(57) ABSTRACT

A pendulum device is used to test the rolling resistance of a material. The device includes a rolling unit for contact with the material being tested, an assembly for initiating pendulum motion of the device, and measuring the amplitude of the pendulum motion over time. The rate of decrease of the amplitude of the pendulum motion is a measure of the rolling resistance of the material.

20 Claims, 5 Drawing Sheets

PENDULUM ROLLING RESISTANT TEST

TECHNICAL FIELD

The invention relates to apparatus for testing the rolling resistance of materials.

BACKGROUND

For product comparison between competitors, and for researching ways to improve elastomeric products, a means is needed for measuring the rolling resistance of products such as conveyor belts, and elastomeric components such as plies or tread used in pneumatic tires. In the prior art, most apparatus and methods for measuring rolling resistance are directed at measuring components of rolling resistance such as hysteresis, G', modulus and the like. Using these parameters, an approximation of rolling resistance can be obtained.

The advantage of approximating rolling resistance based on related parameters is that only very small amounts of material are needed to measure the related parameters. The disadvantage is that the measured parameters do not always interact the same way in different materials to provide an accurate estimation of rolling resistance, and there is no way to predict the contribution of the various parameters in a specific product construction, and the approximations are sometimes incorrect by a substantial margin.

Accordingly, it is an object of the present invention to provide a method and apparatus for directly measuring the rolling resistance of a material, especially an elastomeric material, using a relatively small sample of the material.

1. Background Art

At the annual meeting of the Adhesion Society, held, in Savannah, Ga., Feb. 22–25, 1998, Professor M Chaudhury of Leheigh University presented a poster describing research in which an oscillating rubber roller was used to study adhesion on flat surfaces, using the energy expended as the roller rocked backwards and forwards on a chemically-modified flat surface to measure the difference between energy loss in breaking contact and energy gained on making contact.

Rubber covered rollers have been described by M Hannah, Quart.J.Mech.Appl.Math., 4, 95–105 (1951); G. J. Parish, Brit.J.Appl.Phys., 9, 158–161 (1958); G. J. Parish, Brit.J.Appl.Phys., 9, 428–433 (1958); G. J. Parish, Brit.J.Appl.Phys.12,333–335 (1961); M. Barquins and Efelder, Kautschuk u. Gummi 43,no.2, 114–117(1990); F. Zeppernick, Gummi Fasern Kunststoffs 44, 654(1991) to 46,580(1993).

2. Disclosure of Invention

An apparatus for measuring the rolling resistance of a substrate comprises a rolling means for rolling contact with a surface to be measured, an arm attached to the rolling means and extending downward from said rolling means to free space below the rolling means, a swing weight integral with or attached to the arm distal from the rolling means and in the free space, and measuring means located near the free space for measuring the location of the swing weight relative to the measuring means.

The apparatus may further comprise a lever attached to the rolling means for controlling the initial amplitude of the swing weight when a rolling resistance measurement is taken.

In the illustrated embodiment, the rolling means is a cylinder, and the arm extends at substantially 90° horizontally outward from the mass center of the rolling means, and is further directed downward to a location below the rolling means, whereby the swing weight is located substantially directly below the rolling means.

The swing weight may be round or may be made having flat surfaces.

The measuring means is selected from the group comprising sound and light and the apparatus may further comprise means for collecting data from the measuring means, a computer for storing and analyzing the data, and means for outputting results.

Also provided is a method for measuring the rolling resistance of a substrate comprising the steps of (a) providing an apparatus for measuring the rolling resistance of a substrate, said apparatus comprising a rolling means for rolling contact with a surface to be measured, an arm attached to the rolling means, the arm extending downward from the rolling means to free space below the rolling means, a swing weight integral with or attached to the arm distal from the rolling means and in the free space, and measuring means located near said free space for measuring the location of the swing weight relative to the measuring means, and placing the apparatus on a substrate to be measured, (b) setting the swing weight in pendulum motion while the rolling means rolls back and forth on the substrate, (c) measuring the amplitude of the motion of the swing weight for a period of time sufficient to determine the damping rate of the substrate, and (d) correlating the damping rate of the substrate with the rolling resistance of the substrate. The method may further comprise the step of using a lever attached to the rolling means for starting the motion of the swing weight and the rolling means by holding the lever down and releasing the lever such that gravity initiates the motion and the lever controls the initial amplitude of the motion by its length.

The swing weight may be selected to be a round swing weight or a swing weight with flat sides. When a round swing weight is selected, radar is the preferred means of measuring the position of the swing weight, and when flat sides are on the swing weight, the means for measuring the position of the swing weight may be means using sound or light.

The method may further comprise the steps of (a) creating a data base of damping rates for substrates tested, (b) setting up a ranking system to correlate a damping rate with rolling resistance for a specific substrate using alpha numeric labels representative of each ranking, and (c) comparing subsequent substrates tested for rolling resistance with the ranking based on the damping rates observed for the subsequent substrates.

DETAILED DESCRIPTION OF THE INVENTION

Figure 1:
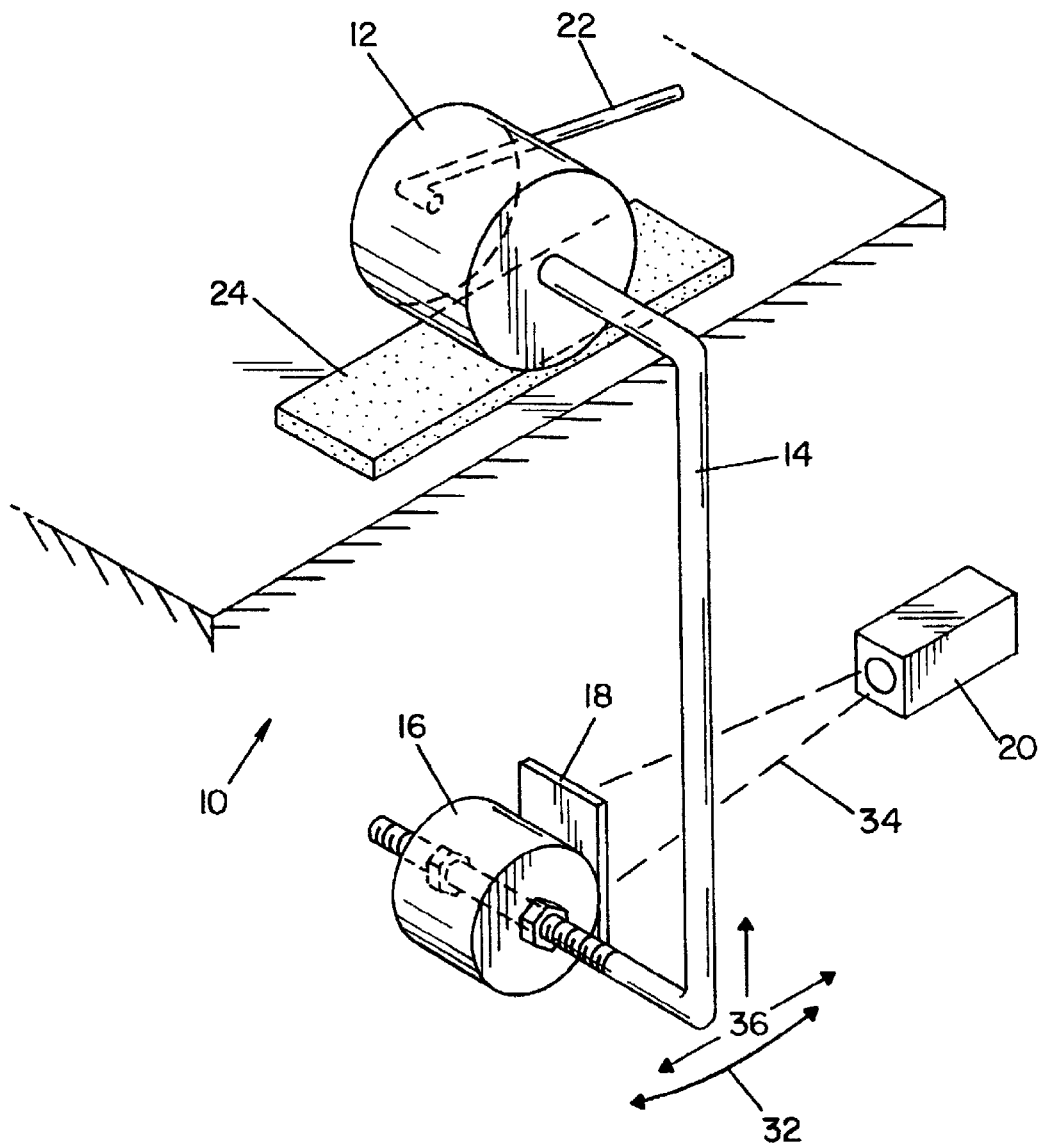
FIG. 1 illustrates an apparatus comprising a rolling means, a swing weight, and a measuring means.

With reference now to FIG. 1, a portion of the apparatus of the invention 10 which contacts the material on which a rolling resistance measurement is being made, and the means of measuring the amplitude of movement of the apparatus is illustrated. The sample (substrate) 24 for which rolling resistance data is to be obtained, is placed on a flat surface and the rolling means 12 of the apparatus is placed on the substrate 24 whereby an arm 14 connected to the rolling means 12 extends downward from rolling means 12 to a free space 36 below the substrate 24 and the rolling means 12. In the illustrated embodiment, a swing weight 16 is connected to arm 14 at a point distal from rolling means 12. A measuring device 20 is fixed in position in the proximity of swing weight 16.

Those skilled in the art will recognize that swing weight 16 is not needed if arm 14 has a concentration of mass distal from rolling means 12.

This portion of the apparatus 10 operates by sewing the swing weight (or the distal end of arm 14) in motion, causing the rolling means 12 to rock back and forth in contact with substrate 24.

The position of the swing weight 16 relative to roller 12 affects the distribution of pressure exerted by roller 12 on a substrate 24. It is believed that the best results are obtained if the pressure distribution of roller 12 is substantially even on substrate 24. To this end, in the manufacture of apparatus 10, a Tekscan® sensor mat was used to measure the pressure distribution of roller 12, and the information obtained was used to adjust the position of swing weight 16 until an even distribution was achieved. Those skilled in the art will recognize that in embodiments of the apparatus where the position of swing weight 16 is not adjustable, this technique can be used to develop a prototype having even pressure distribution, and subsequent apparatus can be made to the same specifications as the prototype.

A lever 22 may be connected to rolling means 12 in order to standardize the movement of the apparatus from sample to sample. For example, a lever 22 of a specific length, when contacted with the flat surface or the substrate 24, will always provide the same amplitude for the rocking motion of rolling means 12 if arm 22 is pushed against the surface or substrate 24, for substrates having the same thickness, and released in the same manner for each sample tested.

Those skilled in the art will recognize that other means may be used for standardizing the motion of the rolling means 12 so that consistent initial input is provided to the apparatus for each sample.

Rolling means 12 may be a cylinder, or a cube with a rounded bottom, or any other shape that provides a consistent rolling or rocking motion in the apparatus.

Swing weight 16 may have any shape which is convenient for obtaining the measurements provided by measuring device 20. For example, swing weight 16 may be round if a radar measuring device is used, but a flat surface 18 is desirable if ultrasonic, laser, or similar measuring devices are used.

It is preferred that the swing weight be substantially directly below rolling means 12, in free space 36 that is sufficient to provide clearance for the motion of the swing weight when rolling means 12 rocks back and forth in the directions of arrow 32. In the illustrated embodiment, arm 14 extends from rolling means 12 at a 90° angle for a distance sufficient to clear the edge of the flat surface on which the substrate 24 is placed, then extends vertically downward at a 90° angle. An additional 90° angle in arm 14, substantially parallel to portion of the arm extending from rolling means 12, puts the distal end of arm 14 substantially vertically below rolling means 12.

Those skilled in the art will recognize that arm 14 may be provided in a semicircle, or some portion of a circle, or for that matter a meandering shape, which eventually brings the distal end of arm 14 substantially vertically below rolling means 12.

As discussed above, measuring device 20 may be any non-contact measuring device known in the art, and the swing weight 16 may be modified or shaped to accommodate whatever measuring device 20 is used.

Figure 2:
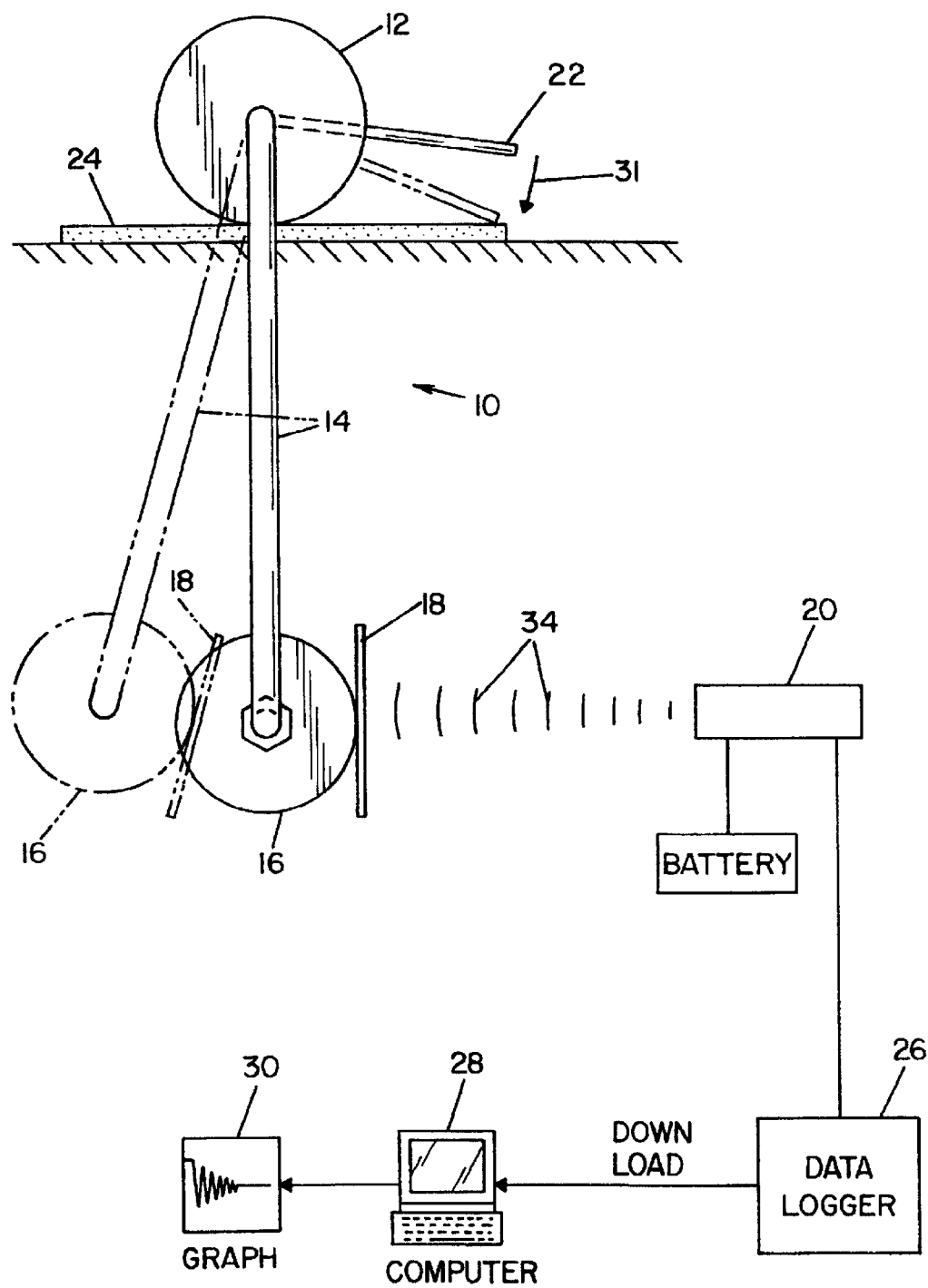
FIG. 2 illustrates motion of the apparatus of FIG. 1 and means for measuring the motion and collecting data.

With reference now to FIG. 2, the movement of arm 14 is illustrated in phantom lines when lever 22, also in phantom lines, is pressed against substrate 24 on the flat surface on which rolling means 12 and substrate 24 is placed. The length of lever 22 determines the distance, or the length of path 31, which determines the maximum range of motion of rolling means 12 on substrate 24.

Measuring device 20 is illustrated as bouncing sound waves or light waves 34 off flat surface 18, whereby the echo or reflection of the waves is detected by measuring device 20 and used to measure the distance between flat surface 18 and measuring device 20. The range of motion of swing weight 16, or amplitude, is a measure of how far rolling means 12 is rocking back and forth on substrate 24. If substrate 24 has a high rolling resistance, this amplitude decreases rapidly, whereas if substrate 24 has a low rolling resistance, this amplitude decreases more slowly as air resistance, and the rolling resistance of the substrate, slowly brings the pendulum motion of the swing weight 16 to a stop. The rate of decrease of the pendulum motion is a measure of the rolling resistance of substate 24.

The motion measurements collected by measuring device 20 are transferred to a data logger 26 where the data is saved. The data may be downloaded from the data logger 26 during the test, or at some time after the test has been run. A computer 28 may be used to calculate variances in condition to standardize the results, and to provide an output 30, for example, a graph of the motion.

Figure 3:
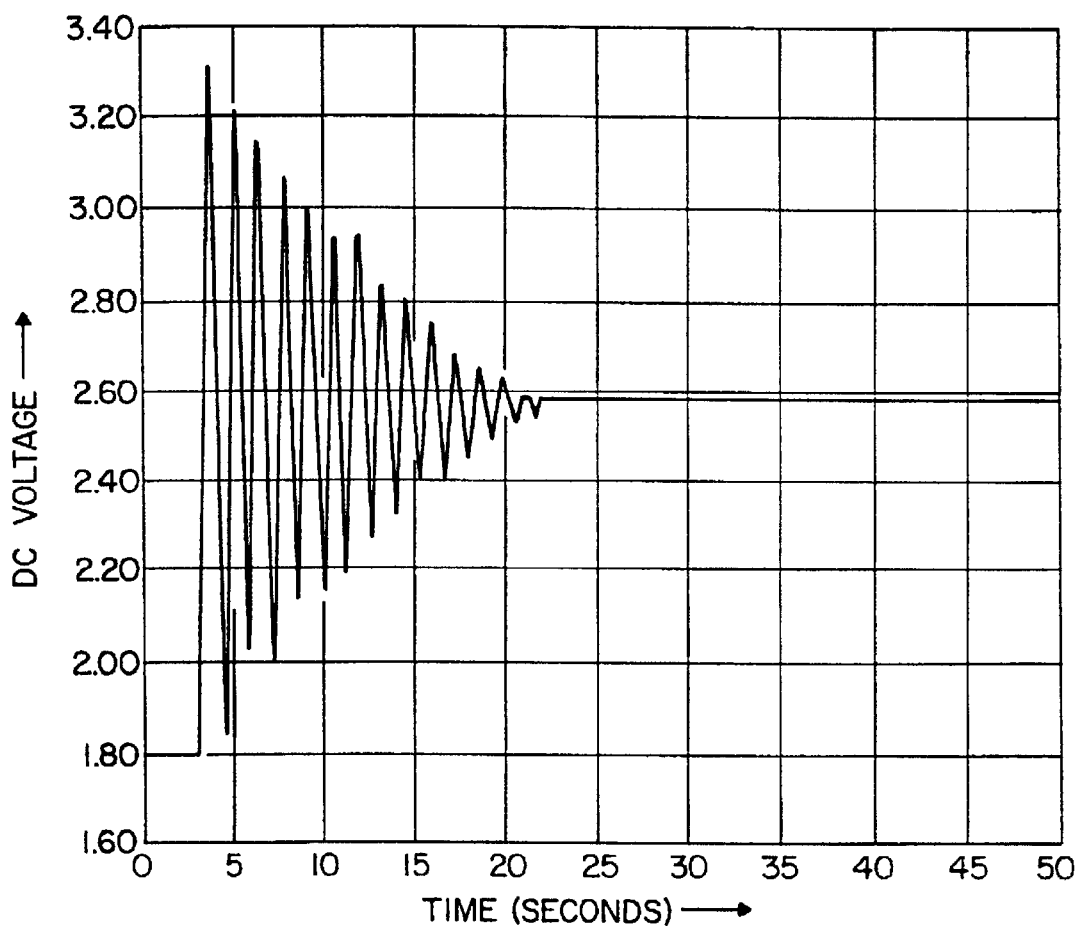
FIG. 3 illustrates oscillation data for a first test substrate.
Figure 4:
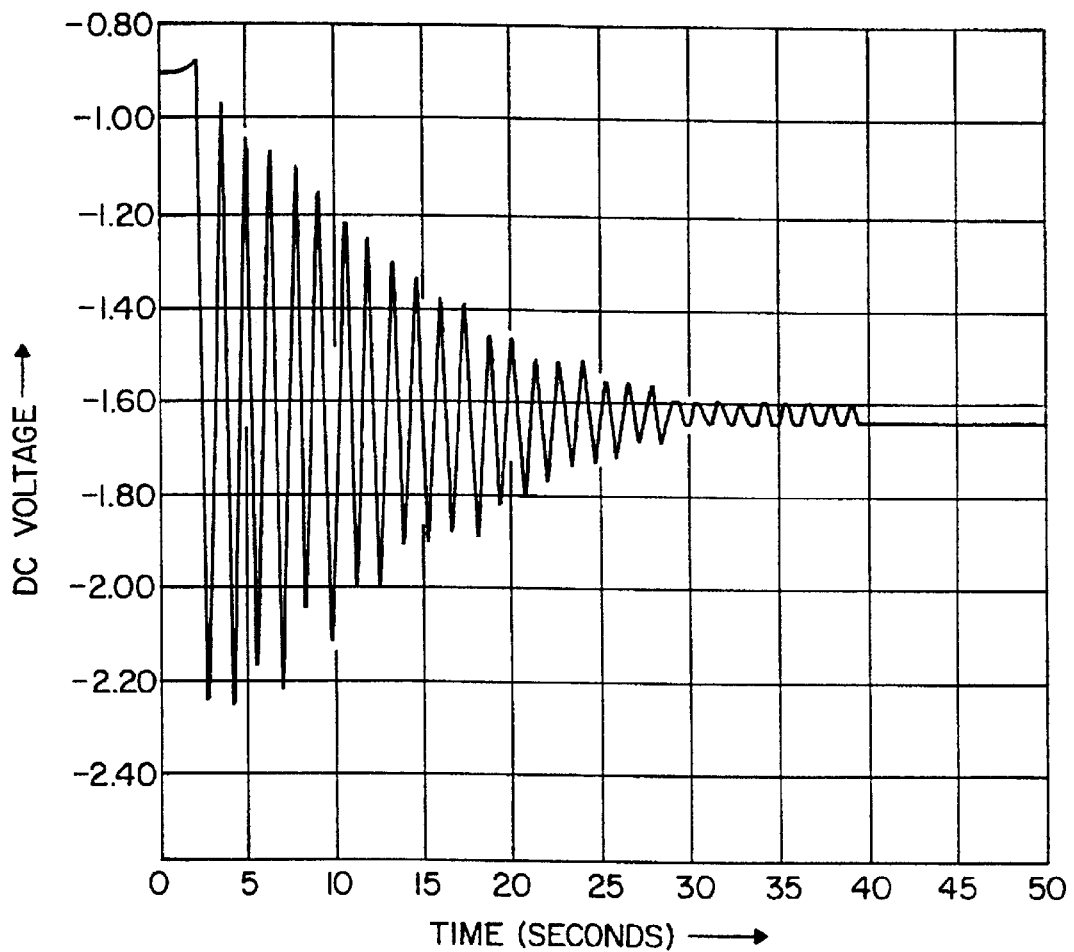
FIG. 4 illustrates oscillation data for a second test substrate.
Figure 5:
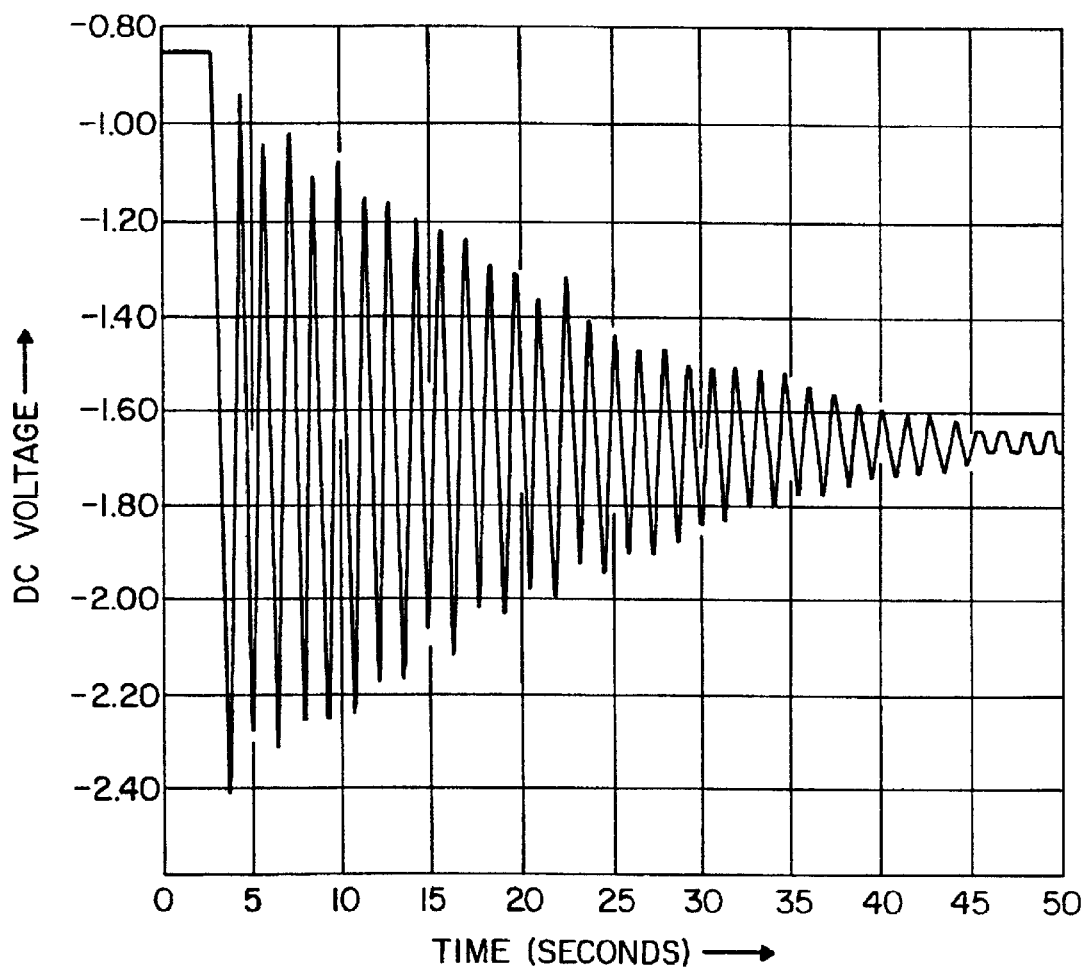
FIG. 5 illustrates oscillation data for a third test substrate.

FIG. 3 illustrates the range of motion of swing weight 16, as interpreted by measuring device 20, in dc voltage. As can be seen on the graph, measuring device 20 has not been zeroed, but the voltage output, from lowest to highest, is an indication of the amplitude of the motion. The rate of decrease in amplitude is illustrated by the reduction of the amplitude over the period of time indicated horizontally on the graph. For example, in FIG. 3, the amplitude is substantially zero after about 20 seconds. By comparison, the substrate tested in FIG. 4 shows that the amplitude of the swing weight has reached substantially zero at about 30 seconds. By further comparison, the substrate tested as illustrated in FIG. 5 showed an amplitude of substantially zero after about 45 seconds.

The apparatus of the invention can be used to provide estimates of energy loss due to rolling friction in rubber sheets or blocks, or in substrates comprising composites, for example cord reinforced belts. The device can be used on a desk or a laboratory bench top.

What is claimed is:

1. An apparatus for measuring the rolling resistance of a substrate, said apparatus comprising
   (a) a rolling means for rolling contact with a surface to be measured;
   (b) an arm attached to said rolling means, said arm extending downward from said rolling means to free space below said rolling means;
   (c) a swing weight integral with or attached to said arm distal from said rolling means and in said free space, the rolling means, arm and swing weights forming a pendelum; and (d) measuring means located near said free space for measuring the location of said swing weight relative to said measuring means.

2. The apparatus of claim 1 further comprising a lever attached to said rolling means.

3. The apparatus of claim 1 wherein said rolling means is a cylinder.

4. The apparatus of claim 1 wherein said arm extends at substantially 90° horizontally outward from the mass center of said rolling means, and is further directed downward to a location vertically below said rolling means, whereby said swing weight is located substantially directly below said rolling means.

5. The apparatus of claim 1 wherein said swing weight is round.

6. The apparatus of claim 1 wherein said swing weight has a flat surface.

7. The apparatus of claim 1 wherein said measuring means is selected from the group comprising sound and light.

8. The apparatus of claim 1 further comprising means for collecting data from said measuring means, a computer for storing and analyzing said data, and means for outputting results.

9. A method for measuring the rolling resistance of a substrate comprising the steps of (a) providing an apparatus for measuring the rolling resistance of a substrate, said apparatus comprising a rolling means for rolling contact with a surface to be measured, an arm attached to said rolling means, said arm extending downward from said rolling means to free space below said rolling means, a swing weight integral with or attached to said arm distal from said rolling means and in said free space, and measuring means located near said free space for measuring the location of said swing weight relative to said measuring means, and placing said apparatus on a substrate to be measured;

(b) setting said swing weight in pendulum motion while said rolling means rolls back and forth on said substrate;

(c) measuring the amplitude of the motion of said swing weight for a period of time sufficient to determine the damping rate of said substrate;

(d) correlating the damping rate of said substrate with the rolling resistance of said substrate.

10. The method of claim 9 further comprising the step of using a lever attached to said rolling means for starting the motion of said swing weight and said rolling means by holding said lever down and releasing said lever such that gravity initiates said motion and said lever controls the initial amplitude of said motion by its length.

11. The method of claim 9 which comprises the further step of selecting a round swing weight for said apparatus.

12. The method of claim 11 comprising the further step of selecting the means of measuring the position of a swing weight as radar.

13. The method of claim 9 which comprises the further step of selecting a swing weight having flat surfaces for said apparatus.

14. The method of claim 13 comprising the further step of selecting the means for measuring the position of said swing weight from the group comprising sound and light.

15. The method of claim 9 comprising the further steps of (a) creating a database of damping rates for compounds tested (b) setting up a ranking system to correlate a damping rate with rolling resistance for a specific substrate using alpha numeric labels representative of each ranking, and (c) comparing subsequent substrates tested for rolling resistance with said ranking based on the damping rates observed for said subsequent substrates.

16. An apparatus for measuring the rolling resistance of a substrate, said apparatus comprising:

(a) rolling means for rolling contact with a surface to be measured, an arm attached to the rolling means, the arm extending downward from the rolling means to free space below the rolling means, a swing weight integral with or attached to the arm distal from the rolling means and in the free space;

(b) means for setting the swing weight in pendulum motion while the rolling means rolls back and forth on the substrate;

(c) means for measuring the amplitude of the motion of the swing weight for a period of time sufficient to determine the damping rate of the substrate;

(d) means correlating the damping rate of the substrate with the rolling resistance of the substrate.

17. An apparatus of claim 16, wherein the means of measuring the position of the swing weight comprises radar.

18. An apparatus of claim 16, wherein the means for measuring the position of the swing weight is selected from a group comprising sound and light.

19. An apparatus of claim 16, wherein further comprising:
a lever attached to the rolling means for starting the motion of the swing weight and the rolling means.

20. An apparatus of claim 16 further comprising:
means for creating a database of damping rates for compounds tested;
means for setting up a ranking system to correlate a damping rate with rolling resistance for a specific substrate using alpha numeric labels representative of each ranking; and
means for comparing subsequent substrates tested for rolling resistance with the ranking based on the damping rates observed for the subsequent substrates.

* * * * *

UNITED STATES PATENT AND TRADEMARK OFFICE
CERTIFICATE OF CORRECTION

PATENT NO.    : 6,494,076 B1
DATED         : December 17, 2002
INVENTOR(S)   : Alan Neville Gent et al.

It is certified that error appears in the above-identified patent and that said Letters Patent is hereby corrected as shown below:

<u>Title page,</u>
Item [54], the title reads: "PENDULUM ROLLING RESISTANT TEST" should read -- PENDULUM ROLLING RESISTANCE TEST --

Signed and Sealed this

Tenth Day of June, 2003

JAMES E. ROGAN
*Director of the United States Patent and Trademark Office*